US012672929B2

(12) United States Patent　　　　(10) Patent No.:　US 12,672,929 B2
Kabakci et al.　　　　　　　　　　　(45) Date of Patent:　　Jul. 7, 2026

(54) FLEXIBLE URETEROSCOPE (fURS) HAPTIC FEEDBACK MECHANISM FOR A ROBOTIC-ASSISTED RETROGRADE INTRA RENAL SURGICAL (RA-RIRS) SYSTEM AND ASSOCIATED METHOD(S) THEREOF

(71) Applicant: ELMED ELEKTRONIK VE MEDIKAL SAN. TIC. A.S., Ankara (TR)

(72) Inventors: Ahmet Sinan Kabakci, Ankara (TR); Erhan Koruk, Ankara (TR)

(73) Assignee: ELMED ELEKTRONIK VE MEDIKAL SAN. TIC. A.S., Ankara (TR)

( * ) Notice: Subject to any disclaimer, the term of this patent is extended or adjusted under 35 U.S.C. 154(b) by 202 days.

(21) Appl. No.: 18/599,567

(22) Filed: Mar. 8, 2024

(65) Prior Publication Data

US 2024/0299112 A1　　Sep. 12, 2024

Related U.S. Application Data

(60) Provisional application No. 63/489,449, filed on Mar. 10, 2023.

(51) Int. Cl.
*A61B 34/00*　　　(2016.01)
*A61B 34/30*　　　(2016.01)
　　　(Continued)

(52) U.S. Cl.
CPC .............. *A61B 34/76* (2016.02); *A61B 34/25* (2016.02); *A61B 34/37* (2016.02); *A61B 34/74* (2016.02);
　　　(Continued)

(58) Field of Classification Search
CPC ......... A61B 34/76; A61B 34/25; A61B 34/37; A61B 34/74; A61B 2034/301; A61B 2034/303; A61B 2090/064; A61B 34/30
See application file for complete search history.

(56) References Cited

U.S. PATENT DOCUMENTS

2020/0405375 A1* 12/2020 Shelton, IV ....... A61B 18/1815
2024/0245472 A1* 7/2024 Konduri ................. A61B 34/37
(Continued)

FOREIGN PATENT DOCUMENTS

WO　WO-2023180891 A1 * 9/2023　............ B25J 9/1689
WO　WO-2023230146 A1 * 11/2023　............ A61B 34/30
(Continued)

OTHER PUBLICATIONS

Gauhar, V., Traxer, O., Cho, S. Y., Teoh, J. Y., Sierra, A., Gauhar, V., Sarica, K., Somani, B., & Castellani, D. (2022). Robotic Retrograde Intrarenal Surgery: A Journey from "Back to the Future". Journal of clinical medicine, 11(18), 5488. https://doi.org/10.3390/jcm11185488 (Year: 2022).*

*Primary Examiner* — Carl H Layno
*Assistant Examiner* — Heidi A Hilsmier
(74) *Attorney, Agent, or Firm* — Ashkan Najafi

(57)　　　　　ABSTRACT

A fURS haptic feedback mechanism includes a sensing unit configured to be retrofitted to an existing controlled section of a robotic-assisted retrograde intra renal surgical (RA-RIRS) system that manipulates an existing fURS shaft. The sensing unit includes a fURS tension detection mechanism configured to detect tension at the existing fURS shaft during a RA-RIRS surgical procedure, and a fURS tension interpretation mechanism configured to receive, evaluate, and quantify the detected tension. The fURS tension interpretation mechanism is further configured to visually display a quantified intensity level of the detected tension at the existing fURS shaft, and emit mechanical feedback, at an (Continued)

existing control handle of the existing RA-RIRS system, the quantified intensity level of the detected tension at the existing fURS shaft.

13 Claims, 9 Drawing Sheets

(51) Int. Cl.
    *A61B 34/37*          (2016.01)
    *A61B 90/00*          (2016.01)

(52) U.S. Cl.
    CPC ... *A61B 2034/301* (2016.02); *A61B 2034/303* (2016.02); *A61B 2090/064* (2016.02)

(56) References Cited

U.S. PATENT DOCUMENTS

| | | | |
|---|---|---|---|
| 2025/0049293 A1 * | 2/2025 | Shelton, IV | A61B 90/39 |
| 2025/0319587 A1 * | 10/2025 | Bajo | B25J 9/1607 |
| 2025/0339012 A1 * | 11/2025 | Ouyang | A61B 1/00032 |

FOREIGN PATENT DOCUMENTS

| | | | | |
|---|---|---|---|---|
| WO | WO-2024018060 A1 * | 1/2024 | | A61B 34/30 |
| WO | WO-2024141903 A1 * | 7/2024 | | A61B 34/30 |

* cited by examiner

Software Flowchart

FLEXIBLE URETEROSCOPE (fURS) HAPTIC FEEDBACK MECHANISM FOR A ROBOTIC-ASSISTED RETROGRADE INTRA RENAL SURGICAL (RA-RIRS) SYSTEM AND ASSOCIATED METHOD(S) THEREOF

CROSS REFERENCE TO RELATED APPLICATIONS

This is a non-provisional patent application that claims priority to and benefit of co-pending U.S. provisional patent application No. 63/489,449 filed Mar. 10, 2023, which is incorporated by reference herein in its entirety.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND

Technical Field

Exemplary embodiment(s) of the present disclosure relate to haptic feedback mechanisms used with flexible ureteroscopy (fURS) procedures and, more particularly, to a specially configured flexible ureteroscope (fURS) haptic feedback mechanism for providing, on a display screen (monitor), (1) visual feedback of the tension levels, as well as providing, on at least one control handle, (2) haptic feedback of the tension levels. Thus, both the visual feedback and the haptic feedback occur at user interfaces of a robotic-assisted retrograde intra renal surgical (RA-RIRS) system.

Prior Art

Retrograde Intra Renal Surgery (RIRS) with flexible ureteroscopy (fURS) has become widespread in the endourology field for the treatment of kidney stones. We have invented and patented a robot for robotic-assisted RIRS (RA-RIRS) as disclosed in U.S. Pat. No. 10,219,867, incorporated by reference herein in its entirety. Such a robotic system is very successful. However, it does not provide haptic feedback. If during a RA-RIRS operation, the surgeon is able to feel some haptic feedback from the shaft of the flexible ureteroscope, the surgeon can determine if there is a stricture, an obstruction, or a difficulty because of any spasms or anatomical or physiological reasons in the urinary tract. Unfortunately, a generic and unquantified haptic feedback is not useful because the surgeon must rely on conjecture to quantify and visualize the extent of the stricture or obstruction based on a subjective interpretation of the haptic feedback characteristics. This is difficult to achieve with a level of high certainty.

For example, a robotic device used during a RA-RIRS procedure has a risk of perforation of the ureter if there is no feedback for the fURS tensions at the control handle of fURS. During the RA-RIRS procedures, the surgeon can follow the operation only thru a video image of the fURS. Such visual information is not enough to detect the requisite characteristics of any stricture or obstruction or any difficulty in the urinary tract. Even if the video image looks good, there is a risk of engaging the ureter to the shaft of fURS and the urinary tract may be damaged (perforated) if the surgeon robotically moves further the fURS shaft. To avoid those risks, such haptic feedback should be given to the surgeon.

For example, conventional haptic feedback mechanisms have been proposed for a fURS robot that relies on intrarenal pressure and torque on the deflection mechanism at the fURS displacement. Such haptic feedback mechanisms studied haptic feedback from torque on a rotation mechanism and torque on a deflection mechanism during fURS procedures. None of them provided haptic feedback at a shaft (user interface) of the RA-RIRS.

Accordingly, a need remains for a haptic feedback system that can be retrofitted on an existing RA-RIRS system to overcome at least one of the above-noted shortcomings. The exemplary embodiment(s) satisfy such a need by a specially configured flexible ureteroscope (fURS) haptic feedback mechanism that is convenient and easy to use, lightweight yet durable in design, versatile in its applications, and configured for providing haptic feedback at a user interface (robot control shaft) of a RA-RIRS system. The scope of the present disclosure adds a new feature to the robot for RA-RIRS systems so the surgeon can quantify and visualize, with a high level of certainty, the haptic feedback characteristics at the robot's control shaft when performing fURS procedures.

BRIEF SUMMARY OF NON-LIMITING EXEMPLARY EMBODIMENT(S) OF THE PRESENT DISCLOSURE

In view of the foregoing background, it is therefore an object of the non-limiting exemplary embodiment(s) to provide a flexible ureteroscope (fURS) haptic feedback mechanism for providing haptic feedback at an existing robotic-assisted retrograde intra renal surgical (RA-RIRS) system. These and other objects, features, and advantages of the non-limiting exemplary embodiment(s) are provided by a fURS haptic feedback mechanism including a sensing unit configured to be retrofitted to an existing controlled section of a robotic-assisted retrograde intra renal surgical (RA-RIRS) system that manipulates an existing fURS shaft, the sensing unit including a fURS tension detection mechanism being configured to detect tension at the existing fURS shaft, during a RA-RIRS surgical procedure, located at the existing controlled section of the RA-RIRS system, and a fURS tension interpretation mechanism in communication with the fURS tension detection mechanism and being configured to receive, evaluate, and quantify the detected tension. Advantageously, the fURS tension interpretation mechanism is further configured to generate and transmit a visual feedback signal to an existing user-control section of the existing RA-RIRS system and thereby visually display, on an existing display screen of the existing RA-RIRS system, a quantified intensity level of the detected tension at the existing fURS shaft; and a haptic feedback signal to the existing user-control section of the existing RA-RIRS system and thereby mechanically emit, at an existing control handle of the existing RA-RIRS system, the quantified intensity level of the detected tension at the existing fURS shaft. Such a structural configuration yields the new, useful, and unpredicted result of providing, on a display screen (monitor), (1) visual feedback of the tension levels, as well as providing, on at least one control handle, (2) haptic feedback of the tension levels. Thus, both the visual feedback and the haptic feedback occur at user interfaces of a robotic-assisted retrograde intra renal surgical (RA-RIRS) system.

In a non-limiting exemplary embodiment(s), the fURS tension detection mechanism includes a load-cell positioned inside the sensing unit and being configured to detect the detected tension, an arm, and a clamp attached to the arm. Advantageously, such a clamp is configured to directly engage the existing fURS shaft while the arm is communicatively coupled to the load-cell. Advantageously, the arm is directly connected to the clamp and the sensing unit, respectively. Advantageously, the arm has a curvilinear shape and is intercalated between the clamp and the sensing unit. Such a structural configuration yields the new, useful, and unpredicted result of providing, on a display screen (monitor), (1) visual feedback of the tension levels, as well as providing, on at least one control handle, (2) haptic feedback of the tension levels. Thus, both the visual feedback and the haptic feedback occur at user interfaces of a robotic-assisted retrograde intra renal surgical (RA-RIRS) system.

In a non-limiting exemplary embodiment(s), the sensing unit further includes a voltage amplifier, an analog to digital converter (ADC) in communication with the voltage amplifier, a micro-controller unit in communication with the ADC, an adapter for converting transistor-transistor logic (TTL) signals to RS232 simple serial communication signals, a programmable logic controller (PLC) in communication with the adapter, and a human-machine-interface (HMI) in communication with the PLC. The HMI transmits the data to a personal computer (PC). Then, the PC formats the data and presents it as a bar graph on the monitor. Such a structural configuration yields the new, useful, and unpredicted result of providing, on a display screen (monitor), (1) visual feedback of the tension levels, as well as providing, on at least one control handle, (2) haptic feedback of the tension levels. Thus, both the visual feedback and the haptic feedback occur at user interfaces of a robotic-assisted retrograde intra renal surgical (RA-RIRS) system.

In a non-limiting exemplary embodiment(s), the arm has a curvilinear shape and extends distally and upwardly from the sensing unit. The arm terminates at the clamp. Such a structural configuration yields the new, useful, and unpredicted result of providing, on a display screen (monitor), (1) visual feedback of the tension levels, as well as providing, on at least one control handle, (2) haptic feedback of the tension levels. Thus, both the visual feedback and the haptic feedback occur at user interfaces of a robotic-assisted retrograde intra renal surgical (RA-RIRS) system.

In a non-limiting exemplary embodiment(s), the visual feedback signal and the haptic feedback signal are simultaneously transmitted to the existing user-control section of the existing RA-RIRS system. Such a structural configuration yields the new, useful, and unpredicted result of providing, on a display screen (monitor), (1) visual feedback of the tension levels, as well as providing, on at least one control handle, (2) haptic feedback of the tension levels. Thus, both the visual feedback and the haptic feedback occur at user interfaces of a robotic-assisted retrograde intra renal surgical (RA-RIRS) system.

In a non-limiting exemplary embodiment(s), the visual feedback signal is graphically illustrated on the existing display screen. Such a structural configuration yields the new, useful, and unpredicted result of providing, on a display screen (monitor), (1) visual feedback of the tension levels, as well as providing, on at least one control handle, (2) haptic feedback of the tension levels. Thus, both the visual feedback and the haptic feedback occur at user interfaces of a robotic-assisted retrograde intra renal surgical (RA-RIRS) system.

In a non-limiting exemplary embodiment(s), the haptic feedback signal is mechanically emitted at the existing control handle of the existing RA-RIRS system. Such a structural configuration yields the new, useful, and unpredicted result of providing, on a display screen (monitor), (1) visual feedback of the tension levels, as well as providing, on at least one control handle, (2) haptic feedback of the tension levels. Thus, both the visual feedback and the haptic feedback occur at user interfaces of a robotic-assisted retrograde intra renal surgical (RA-RIRS) system.

In a non-limiting exemplary embodiment(s), the fURS tension detection mechanism includes a strain-gauge configured to detect the detected tension. Such a structural configuration yields the new, useful, and unpredicted result of providing, on a display screen (monitor), (1) visual feedback of the tension levels, as well as providing, on at least one control handle, (2) haptic feedback of the tension levels. Thus, both the visual feedback and the haptic feedback occur at user interfaces of a robotic-assisted retrograde intra renal surgical (RA-RIRS) system.

In a non-limiting exemplary embodiment(s), the fURS tension detection mechanism includes a force sensor configured to detect the detected tension. Such a structural configuration yields the new, useful, and unpredicted result of providing, on a display screen (monitor), (1) visual feedback of the tension levels, as well as providing, on at least one control handle, (2) haptic feedback of the tension levels. Thus, both the visual feedback and the haptic feedback occur at user interfaces of a robotic-assisted retrograde intra renal surgical (RA-RIRS) system.

In a non-limiting exemplary embodiment(s), the fURS tension detection mechanism includes a load-cell configured to detect the detected tension. For example, the load cell converts the detection tension (e.g., tension, torque, compression, pressure, etc.) into an output signal. This output signal is then transmitted via a load cable to fURS tension interpretation mechanism where a precise intensity level is measured (quantified). FIGS. 7-9 illustrated the interrelationship between the major electrical components as well as the control logic algorithm for quantifying as well as visually and mechanically providing feedback signals to the user-control section of the RA-RIRS system. Such a structural configuration yields the new, useful, and unpredicted result of providing, on a display screen (monitor), (1) visual feedback of the tension levels, as well as providing, on at least one control handle, (2) haptic feedback of the tension levels. Thus, both the visual feedback and the haptic feedback occur at user interfaces of a robotic-assisted retrograde intra renal surgical (RA-RIRS) system.

In a non-limiting exemplary embodiment(s), the fURS tension detection mechanism includes a torque sensor configured to detect the detected tension. Such a structural configuration yields the new, useful, and unpredicted result of providing, on a display screen (monitor), (1) visual feedback of the tension levels, as well as providing, on at least one control handle, (2) haptic feedback of the tension levels. Thus, both the visual feedback and the haptic feedback occur at user interfaces of a robotic-assisted retrograde intra renal surgical (RA-RIRS) system.

In a non-limiting exemplary embodiment(s), the sensing unit is configured to be mechanically retrofitted directly to the existing fURS shaft. Such a structural configuration yields the new, useful, and unpredicted result of providing, on a display screen (monitor), (1) visual feedback of the tension levels, as well as providing, on at least one control handle, (2) haptic feedback of the tension levels. Thus, both the visual feedback and the haptic feedback occur at user interfaces of a robotic-assisted retrograde intra renal surgical (RA-RIRS) system.

In a non-limiting exemplary embodiment(s), the fURS tension detection mechanism includes an arm and a clamp attached thereto. The clamp is configured to directly engage the existing fURS shaft while the arm is communicatively coupled to the load-cell. Such a structural configuration yields the new, useful, and unpredicted result of providing, on a display screen (monitor), (1) visual feedback of the tension levels, as well as providing, on at least one control handle, (2) haptic feedback of the tension levels. Thus, both the visual feedback and the haptic feedback occur at user interfaces of a robotic-assisted retrograde intra renal surgical (RA-RIRS) system.

There has thus been outlined, rather broadly, the more important features of non-limiting exemplary embodiment(s) of the present disclosure so that the following detailed description may be better understood, and that the present contribution to the relevant art(s) may be better appreciated. There are additional features of the non-limiting exemplary embodiment(s) of the present disclosure that will be described hereinafter and which will form the subject matter of the claims appended hereto.

BRIEF DESCRIPTION OF THE NON-LIMITING EXEMPLARY DRAWINGS

The novel features believed to be characteristic of non-limiting exemplary embodiment(s) of the present disclosure are set forth with particularity in the appended claims. The non-limiting exemplary embodiment(s) of the present disclosure itself, however, both as to its organization and method of operation, together with further objects and advantages thereof, may best be understood by reference to the following description taken in connection with the accompanying drawings in which:

Figure 1:
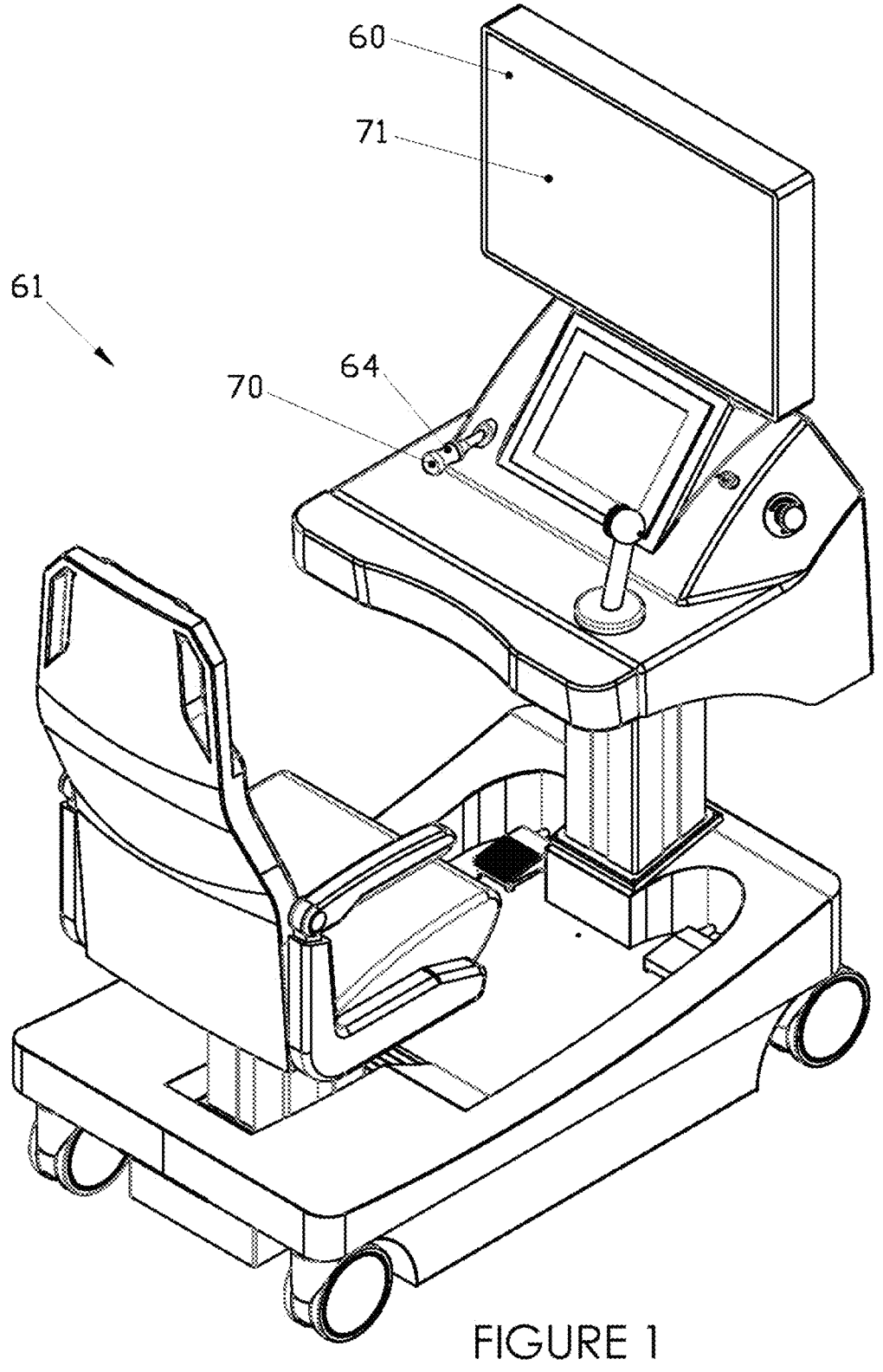
FIG. 1 is a perspective environmental view of a portion of a fURS haptic feedback mechanism showing contemporaneous visual and haptic feedback at user-control interfaces (e.g., display screen and control handle) of a RA-RIRS system, in accordance with a non-limiting exemplary embodiment of the present disclosure.
Figure 2:
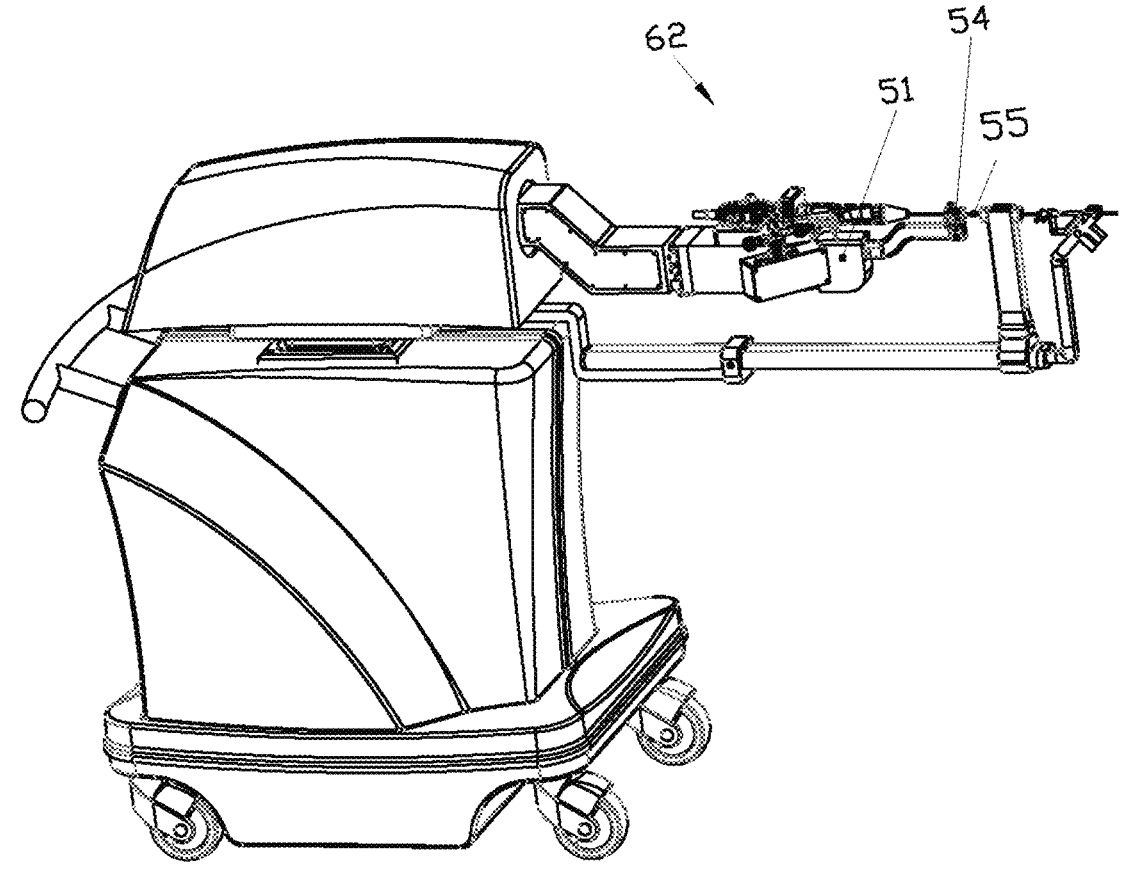
FIG. 2 is another perspective environmental view of a portion of a fURS haptic feedback mechanism including a sensing unit, an arm, and a clamp attached to an existing robot manipulator (user-controlled section) of a RA-RIRS system.
Figure 3:
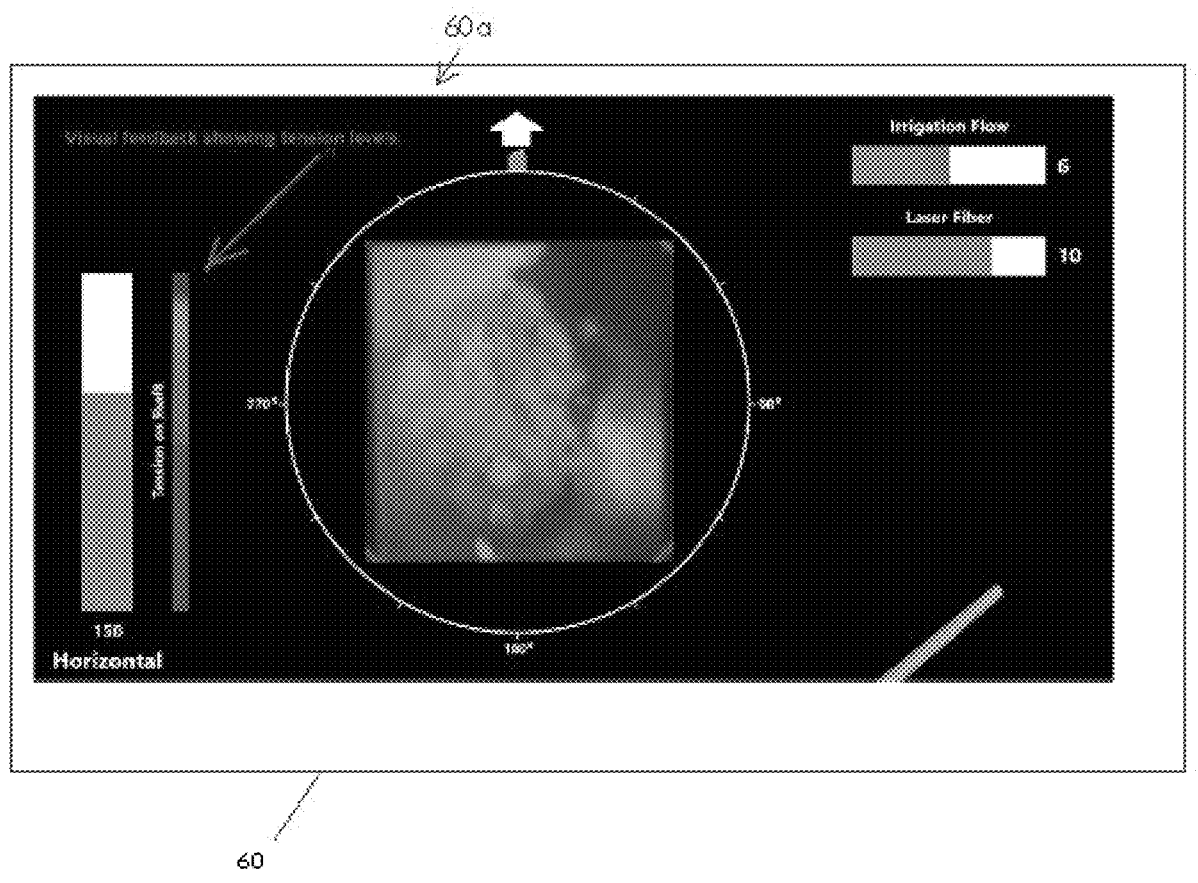
FIG. 3 is a front elevational view showing, on a display screen of the RA-RIRS system, visual feedback of a tension level associated with the existing robot manipulator shown in FIG. 2.
Figure 4:
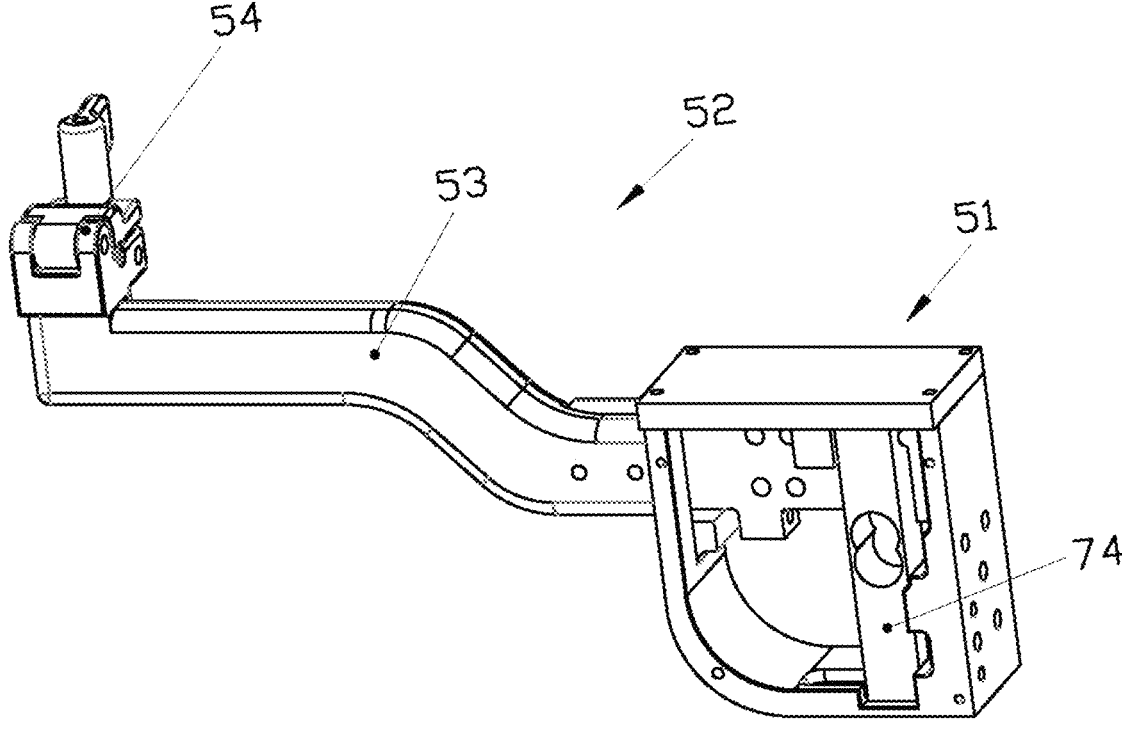
FIG. 4 is an enlarged perspective view of the sensing unit, the arm, and the clamp shown in FIG. 2.
Figure 5:
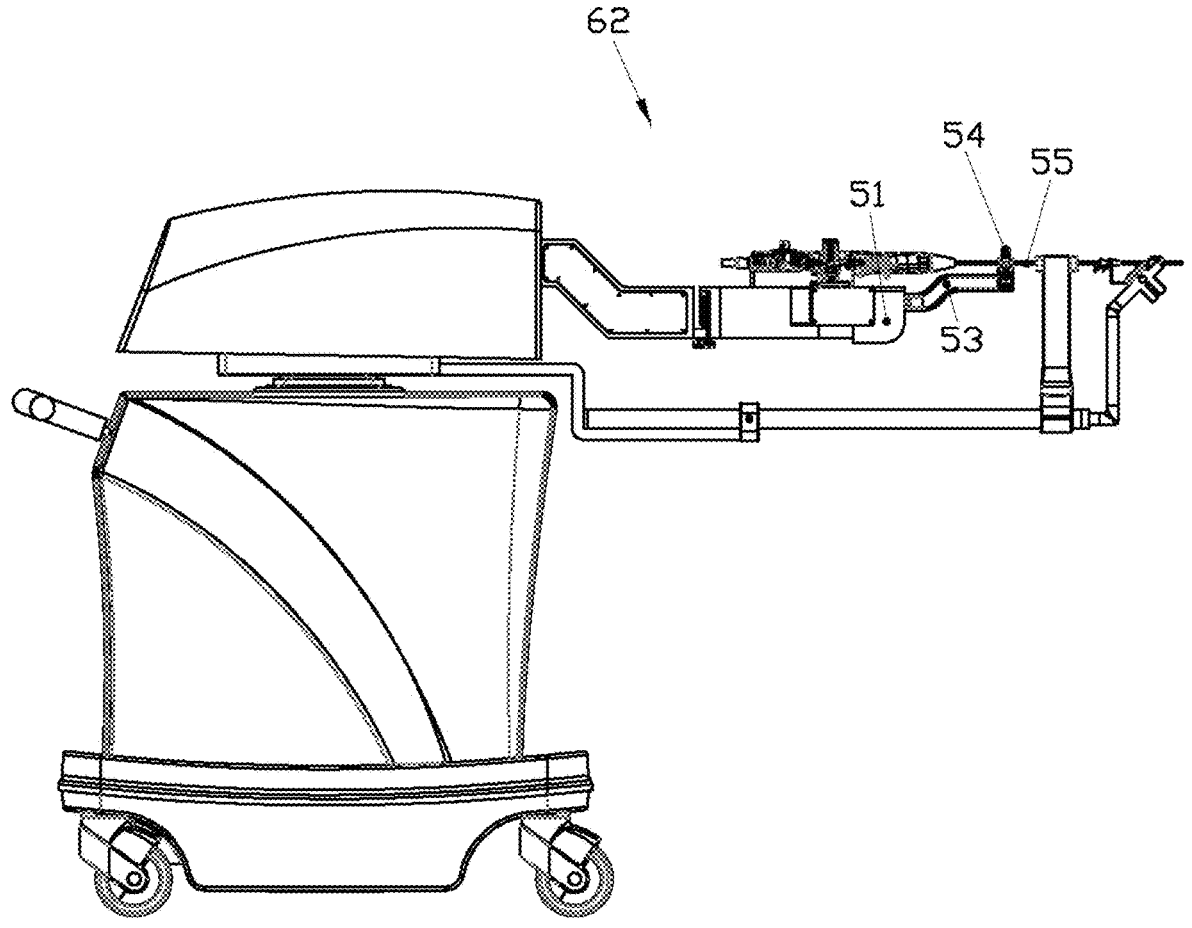
FIG. 5 is a side elevational view of the portion of a fURS haptic feedback mechanism including a sensing unit, an arm, and a clamp attached to an existing robot manipulator (user-controlled section) of a RA-RIRS system, as shown in FIG. 2.
Figure 6:
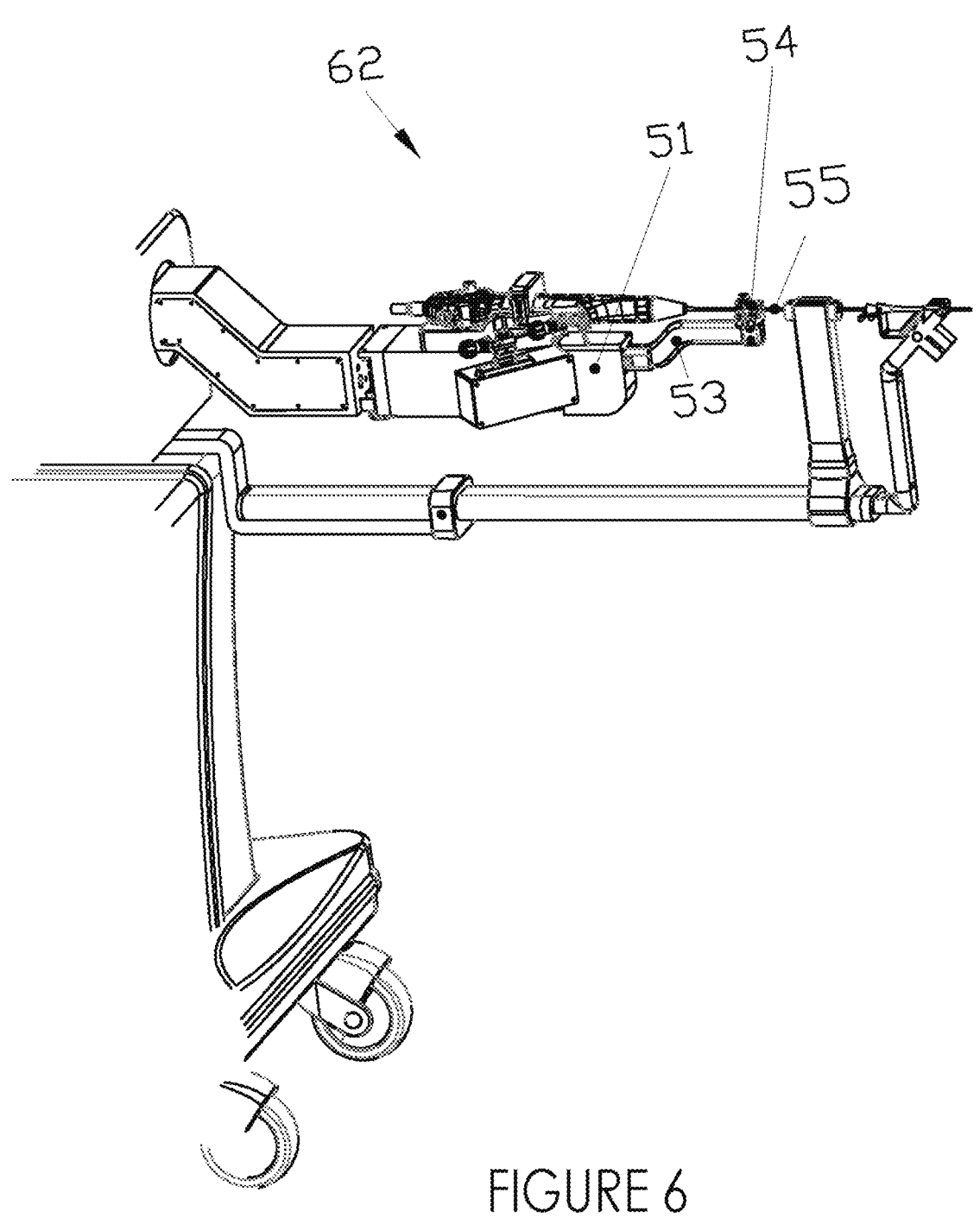
FIG. 6 is another perspective environmental view of the portion of a fURS haptic feedback mechanism including a sensing unit, an arm, and a clamp attached to an existing robot manipulator (user-controlled section) of a RA-RIRS system, as shown in FIG. 2.

Those skilled in the art will appreciate that the figures are not intended to be drawn to any particular scale; nor are the figures intended to illustrate every non-limiting exemplary embodiment(s) of the present disclosure. The present disclosure is not limited to any particular non-limiting exemplary embodiment(s) depicted in the figures nor the shapes, relative sizes or proportions shown in the figures.

DETAILED DESCRIPTION OF NON-LIMITING EXEMPLARY EMBODIMENT(S) OF THE PRESENT DISCLOSURE

The present disclosure will now be described more fully hereinafter with reference to the accompanying drawings, in which non-limiting exemplary embodiment(s) of the present disclosure is shown. The present disclosure may, however, be embodied in many different forms and should not be construed as limited to the non-limiting exemplary embodiment(s) set forth herein. Rather, such non-limiting exemplary embodiment(s) are provided so that this application will be thorough and complete, and will fully convey the true spirit and scope of the present disclosure to those skilled in the relevant art(s). Like numbers refer to like elements throughout the figures.

The illustrations of the non-limiting exemplary embodiment(s) described herein are intended to provide a general understanding of the structure of the present disclosure. The illustrations are not intended to serve as a complete description of all of the elements and features of the structures, systems and/or methods described herein. Other non-limiting exemplary embodiment(s) may be apparent to those of ordinary skill in the relevant art(s) upon reviewing the disclosure. Other non-limiting exemplary embodiment(s) may be utilized and derived from the disclosure such that structural, logical substitutions and changes may be made without departing from the true spirit and scope of the present disclosure. Additionally, the illustrations are merely representational are to be regarded as illustrative rather than restrictive.

One or more embodiment(s) of the disclosure may be referred to herein, individually and/or collectively, by the term "non-limiting exemplary embodiment(s)" merely for convenience and without intending to voluntarily limit the true spirit and scope of this application to any particular non-limiting exemplary embodiment(s) or inventive concept. Moreover, although specific embodiment(s) have been illustrated and described herein, it should be appreciated that any subsequent arrangement designed to achieve the same or similar purpose may be substituted for the specific embodiment(s) shown. This disclosure is intended to cover any and all subsequent adaptations or variations of other embodiment(s). Combinations of the above embodiment(s), and other embodiment(s) not specifically described herein, will be apparent to those of skill in the relevant art(s) upon reviewing the description.

References in the specification to "one embodiment(s)", "an embodiment(s)", "a preferred embodiment(s)", "an alternative embodiment(s)" and similar phrases mean that a particular feature, structure, or characteristic described in connection with the embodiment(s) is included in at least an embodiment(s) of the non-limiting exemplary embodiment(s). The appearances of the phrase "non-limiting exemplary embodiment" in various places in the specification are not necessarily all meant to refer to the same embodiment(s).

Directional and/or relationary terms such as, but not limited to, left, right, nadir, apex, top, bottom, vertical, horizontal, back, front and lateral are relative to each other and are dependent on the specific orientation of an applicable element or article, and are used accordingly to aid in the description of the various embodiment(s) and are not necessarily intended to be construed as limiting.

If used herein, "about," "generally," and "approximately" mean nearly and in the context of a numerical value or range set forth means±15% of the numerical.

If used herein, "substantially" means largely if not wholly that which is specified but so close that the difference is insignificant.

A non-limiting exemplary embodiment(s) of the present disclosure is referred to generally in FIGS. 1-9 and is/are intended to provide a specially configured flexible ureteroscope (fURS) haptic feedback mechanism 50 for providing haptic feedback 70 at a user interface (robot control handle 64) of a RA-RIRS system 57. It should be understood that the exemplary embodiment(s) may be used to provide haptic feedback 70 for a variety of RA-RIRS systems, and should not be limited to any particular RA-RIRS system described herein.

Figure 7:
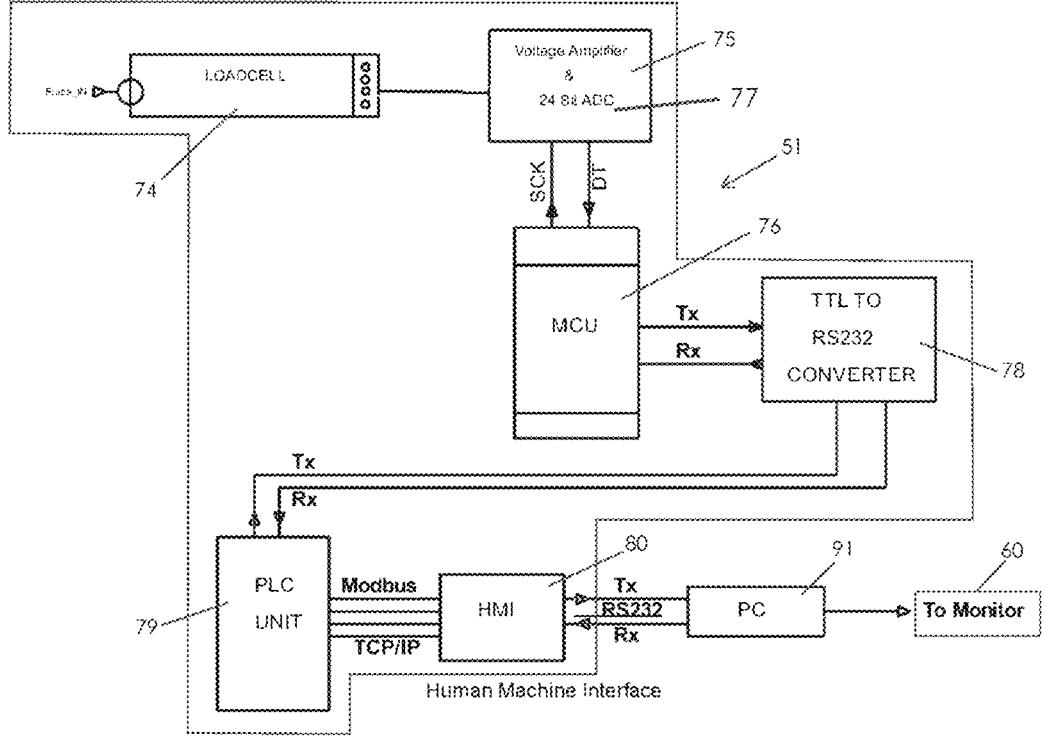
FIG. 7 is a high-level schematic block diagram showing the interrelationship of selected major electronic components of the present disclosure.
Figure 8:
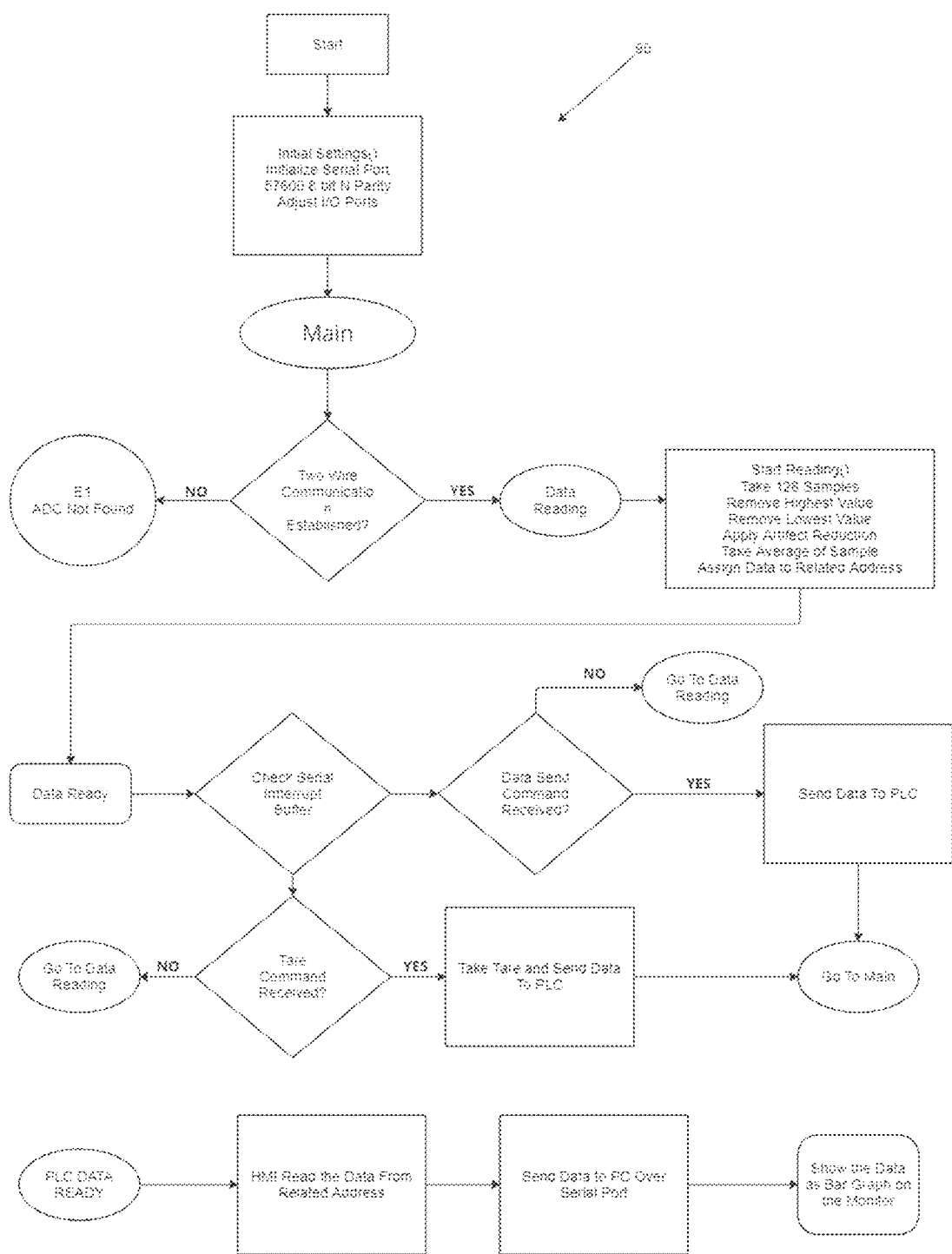
FIG. 8 is a flowchart showing the control logic algorithm of the software module(s) associated with providing both visual and haptic feedback of the tension levels.

Referring generally to FIGS. 1-9, in a non-limiting exemplary embodiment(s), the haptic feedback mechanism 50 includes a sensing unit 51 having a fURS tension detection mechanism 52 including a strain-gauge 85 or a force sensor 86 or a load-cell 74 or a torque sensor 88. The fURS tension detection mechanism 52 further includes an arm 53 with a clamp 54 squeezing a proximal part of the fURS shaft 55 at the controlled section 62 so that the arm 53 detects any tension on the fURS shaft 55, during a surgical procedure, at the controlled section 62 of the RA-RIRS system 57. The sensing unit 51 further has a fURS tension interpretation mechanism 58 to interpret the detected unintended forces (obstruction, structure, etc.) by the fURS tension detection mechanism 52. Upon receiving the unintended forces from one of the aforementioned sensors (e.g., strain-gauge 85 or a force sensor 86 or a load-cell 74 or a torque sensor 88) of the fURS tension detection mechanism 52, the fURS tension interpretation mechanism 58 evaluates, quantifies, and visually illustrates the unintended forces. Advantageously, a visual feedback signal (visual feedback 71) is then generated and transmitted to a graphical user interface 60a displayed on a display screen 60 at a user-control section 61 of the RA-RIRS system 57, which is remotely located from the controlled section 62 of the RA-RIRS system 57. Advantageously, the surgeon can understand with a high level of certainty the characteristics (e.g., intensity, location, etc.) of the remotely detected fURS tension at the controlled section 62 of the RA-RIRS system 57. In addition, there is a mechanical haptic feedback device 63 (e.g., vibration motor 63a) installed at the control handle 64 of the user-control section 61 (user-interface console) of the RA-RIRS system 57. Such a vibration motor 63a starts vibrating the control handle 64 when the detected fURS tension exceeds a predetermined minimum threshold level. Advantageously, the haptic feedback 70 received by the surgeon during the manual operation of the RA-RIRS system 57 is provided as corresponding contemporaneous feedback to the visual feedback 71 selectively, chronologically, or contemporaneously illustrated on the display screen 60 during the RA-RIRS procedures. FIG. 8 illustrates a flowchart 90 of the control logic algorithm for providing the functions of the present disclosure. Such a structural configuration yields the new, useful, and unpredicted result of selectively, chronologically, or contemporaneously providing, on a display screen 60 (monitor), (1) visual feedback 71 of the tension levels, as well as providing, on at least one control handle 64, (2) haptic feedback 70 of the tension levels. Thus, both the visual feedback 71 and the haptic feedback 70 selectively, chronologically, or contemporaneously occur at user interfaces of a robotic-assisted retrograde intra renal surgical (RA-RIRS) system 57.

In a non-limiting exemplary embodiment(s), the entire sensing unit 51 including arm 53 and clamp 54 can be disposable or reusable so they can be sterilized and used many times. Alternately, only the clamp 54 can be disposable or reusable/sterilizable many times. Such a structural configuration yields the new, useful, and unpredicted result of selectively, chronologically, or contemporaneously providing, on a display screen 60 (monitor), (1) visual feedback 71 of the tension levels, as well as providing, on at least one control handle 64, (2) haptic feedback 70 of the tension levels. Thus, both the visual feedback 71 and the haptic feedback 70 selectively, chronologically, or contemporaneously occur at user interfaces of a robotic-assisted retrograde intra renal surgical (RA-RIRS) system 57.

In a non-limiting exemplary embodiment, visual feedback 71 and haptic feedback 70 are simultaneous. Visual feedback 71 is provided as a bar graph or similar display on the GUI 60a display screen 60. Haptic feedback 70 may be provided as a resistive force against the handle 64 movement or a vibration at the handle 64. Such visual feedback 71 and haptic feedback 70 may be selectively provided, chronologically provided, or selectively, chronologically, or contemporaneously provided.

In a non-limiting exemplary embodiment, visual feedback 71 and haptic feedback 70 are not initially simultaneous but overlap in a time period if the actual tension level exceeds a minimum threshold tension level. For example, visual feedback 71 may be initially provided and, if the actual tension level exceeds a minimum threshold tension level (or multiple predetermined and programmable minimum threshold tension levels), then various vibration intensities, vibration patterns, or resistance is/are provided as haptic feedback 70 at the control joystick. In this manner, the visual feedback 71 and haptic feedback 70 are chronological or sequential.

In a non-limiting exemplary embodiment, there are two ways that haptic feedback 70 is provided at the control handle 64. The first way is by reflecting the tension as a resistance to the movement of the control handle 64. In that method, the visual feedback 71 and the haptic feedback 70 will be simultaneous. In the second way, the tension is not reflected as a resistance to the movement of the handle 64, instead, a vibration is given to the handle 64 if the tension exceeds the minimum threshold tension level. In that method, the visual indication will be a real-time display showing the tension level. However, haptic feedback 70 on the handle 64 will not give any handle 64 movement resistance or handle 64 vibration until the minimum threshold tension level is reached. In this manner, the haptic feedback 70 is selectively applied to the control handle 64.

Referring generally to FIGS. 1-9 in general, in a non-limiting exemplary embodiment(s), a flexible ureteroscope (fURS) haptic feedback mechanism 50 for providing contemporaneous haptic feedback 70 and visual feedback 71 at an existing robotic-assisted retrograde intra renal surgical (RA-RIRS) system 57, is disclosed. The fURS haptic feedback mechanism 50 includes a sensing unit 51 configured to be retrofitted to an existing controlled section 62 of a robotic-assisted retrograde intra renal surgical (RA-RIRS) system 57 that manipulates an existing fURS shaft 55. Such a sensing unit 51 includes a fURS tension detection mechanism 52 being configured to detect tension at the existing fURS shaft 55, during a RA-RIRS surgical procedure, located at the existing controlled section 62 of the RA-RIRS system 57. The sensing unit 51 further includes a fURS tension interpretation mechanism 58 in communication with the fURS tension detection mechanism 52 and being configured to receive, evaluate, and quantify the detected tension. Advantageously, the fURS tension interpretation mechanism 58 is further configured to selectively, chronologically, or contemporaneously generate and transmit a visual feedback signal (visual feedback 71) to an existing user-control section 61 of the existing RA-RIRS system 57 and thereby visually display, on an existing display screen 60 of the existing RA-RIRS system 57, a quantified intensity level of the detected tension at the existing fURS shaft 55 (see FIGS. 1 and 3); and a haptic feedback 70 signal to the existing user-control section 61 of the existing RA-RIRS system 57 and thereby mechanically emit, at the existing control handle 64 of the existing RA-RIRS system 57, the quantified intensity level of the detected tension at the existing fURS shaft 55. Such a structural configuration yields the new, useful, and unpredicted result of selectively, chronologically, or contemporaneously providing, on a display screen 60 (monitor), (1) visual feedback 71 of the tension levels, as well as providing, on at least one control handle 64, (2) haptic feedback 70 of the tension levels. Thus, both the visual feedback 71 and the haptic feedback 70 selectively, chronologically, or contemporaneously occur at user interfaces of a robotic-assisted retrograde intra renal surgical (RA-RIRS) system 57.

In a non-limiting exemplary embodiment(s), the fURS tension detection mechanism 52 includes a load-cell 74 positioned inside the sensing unit 51 and being configured to detect the detected tension at shaft 55, an arm 53, and a clamp 54 attached to the arm 53. Advantageously, such a clamp 54 is configured to directly engage the existing fURS shaft 55 while the arm 53 is communicatively coupled to the load-cell 74. Advantageously, the arm 53 is directly connected to the clamp 54 and the sensing unit 51, respectively. Advantageously, the arm 53 has a curvilinear shape and is intercalated between the clamp 54 and the sensing unit 51. Such a structural configuration yields the new, useful, and unpredicted result of selectively, chronologically, or contemporaneously providing, on a display screen 60 (monitor), (1) visual feedback 71 of the tension levels, as well as providing, on at least one control handle 64, (2) haptic feedback 70 of the tension levels. Thus, both the visual feedback 71 and the haptic feedback 70 selectively, chronologically, or contemporaneously occur at user interfaces of a robotic-assisted retrograde intra renal surgical (RA-RIRS) system 57.

In a non-limiting exemplary embodiment(s), referring to FIG. 7, the sensing unit 51 further includes a voltage amplifier 75, an analog to digital converter (ADC 77) in communication with the voltage amplifier 75, a microcontroller unit 76 in communication with the ADC 77, an adapter 78 for converting transistor-transistor logic (TTL) signals to RS232 simple serial communication signals, a programmable logic controller (PLC 79) in communication with the adapter 78, and a human-machine-interface (HMI 80) in communication with the PLC 79. The HMI 80 transmits the data to a personal computer (PC 91). Then, the PC 91 formats the data and presents it as a bar graph (visual feedback 71) on the graphical user interface 60a of the monitor (display screen 60). Such a structural configuration yields the new, useful, and unpredicted result of selectively, chronologically, or contemporaneously providing, on a display screen 60 (monitor), (1) visual feedback 71 of the tension levels, as well as providing, on at least one control handle 64, (2) haptic feedback 70 of the tension levels. Thus, both the visual feedback 71 and the haptic feedback 70 selectively, chronologically, or contemporaneously occur at user interfaces of a robotic-assisted retrograde intra renal surgical (RA-RIRS) system 57.

In a non-limiting exemplary embodiment(s), the arm 53 has a curvilinear shape and extends distally and upwardly from the sensing unit 51. The arm 53 terminates at the clamp 54. Such a structural configuration yields the new, useful, and unpredicted result of selectively, chronologically, or contemporaneously providing, on a display screen 60 (monitor), (1) visual feedback 71 of the tension levels, as well as providing, on at least one control handle 64, (2) haptic feedback 70 of the tension levels. Thus, both the visual feedback 71 and the haptic feedback 70 selectively, chronologically, or contemporaneously occur at user interfaces of a robotic-assisted retrograde intra renal surgical (RA-RIRS) system 57.

In a non-limiting exemplary embodiment(s), the visual feedback signal (visual feedback 71) and the haptic feedback 70 signal are simultaneously (selectively, chronologically, or contemporaneously) transmitted to the existing user-control section 61 (e.g., display screen 60 and control handle 64, respectively) of the existing RA-RIRS system 57. Such a structural configuration yields the new, useful, and unpredicted result of selectively, chronologically, or contemporaneously providing, on a display screen 60 (monitor), (1) visual feedback 71 of the tension levels, as well as providing, on at least one control handle 64, (2) haptic feedback 70 of the tension levels. Thus, both the visual feedback 71 and the haptic feedback 70 selectively, chronologically, or contemporaneously occur at user interfaces of a robotic-assisted retrograde intra renal surgical (RA-RIRS) system 57.

In a non-limiting exemplary embodiment(s), the visual feedback signal 71 (visual feedback) is graphically illustrated on graphical user interface 60a of the existing display screen 60. Such a structural configuration yields the new, useful, and unpredicted result of selectively, chronologically, or contemporaneously providing, on a display screen 60 (monitor), (1) visual feedback 71 of the tension levels, as well as providing, on at least one control handle 64, (2) haptic feedback 70 of the tension levels. Thus, both the visual feedback 71 and the haptic feedback 70 selectively, chronologically, or contemporaneously occur at user interfaces of a robotic-assisted retrograde intra renal surgical (RA-RIRS) system 57.

In a non-limiting exemplary embodiment(s), the haptic feedback 70 signal is mechanically emitted at the existing control handle 64 of the existing RA-RIRS system 57. Such a structural configuration yields the new, useful, and unpredicted result of selectively, chronologically, or contemporaneously providing, on a display screen 60 (monitor), (1) visual feedback 71 of the tension levels, as well as providing, on at least one control handle 64, (2) haptic feedback 70 of the tension levels. Thus, both the visual feedback 71 and the haptic feedback 70 selectively, chronologically, or contemporaneously occur at user interfaces of a robotic-assisted retrograde intra renal surgical (RA-RIRS) system 57.

In a non-limiting exemplary embodiment(s), the fURS tension detection mechanism 52 includes a strain-gauge 85 configured to detect the detected tension at shaft 55 of the fURS RA-RIRS system 57. Such a structural configuration yields the new, useful, and unpredicted result of selectively, chronologically, or contemporaneously providing, on a display screen 60 (monitor), (1) visual feedback 71 of the tension levels, as well as providing, on at least one control handle 64, (2) haptic feedback 70 of the tension levels. Thus, both the visual feedback 71 and the haptic feedback 70 selectively, chronologically, or contemporaneously occur at user interfaces of a robotic-assisted retrograde intra renal surgical (RA-RIRS) system 57.

In a non-limiting exemplary embodiment(s), the fURS tension detection mechanism 52 includes a force sensor 86 configured to detect the detected tension at shaft 55 of the fURS RA-RIRS system 57. Such a structural configuration yields the new, useful, and unpredicted result of selectively, chronologically, or contemporaneously providing, on a display screen 60 (monitor), (1) visual feedback 71 of the tension levels, as well as providing, on at least one control handle 64, (2) haptic feedback 70 of the tension levels. Thus, both the visual feedback 71 and the haptic feedback 70 selectively, chronologically, or contemporaneously occur at user interfaces of a robotic-assisted retrograde intra renal surgical (RA-RIRS) system 57.

Figure 9:
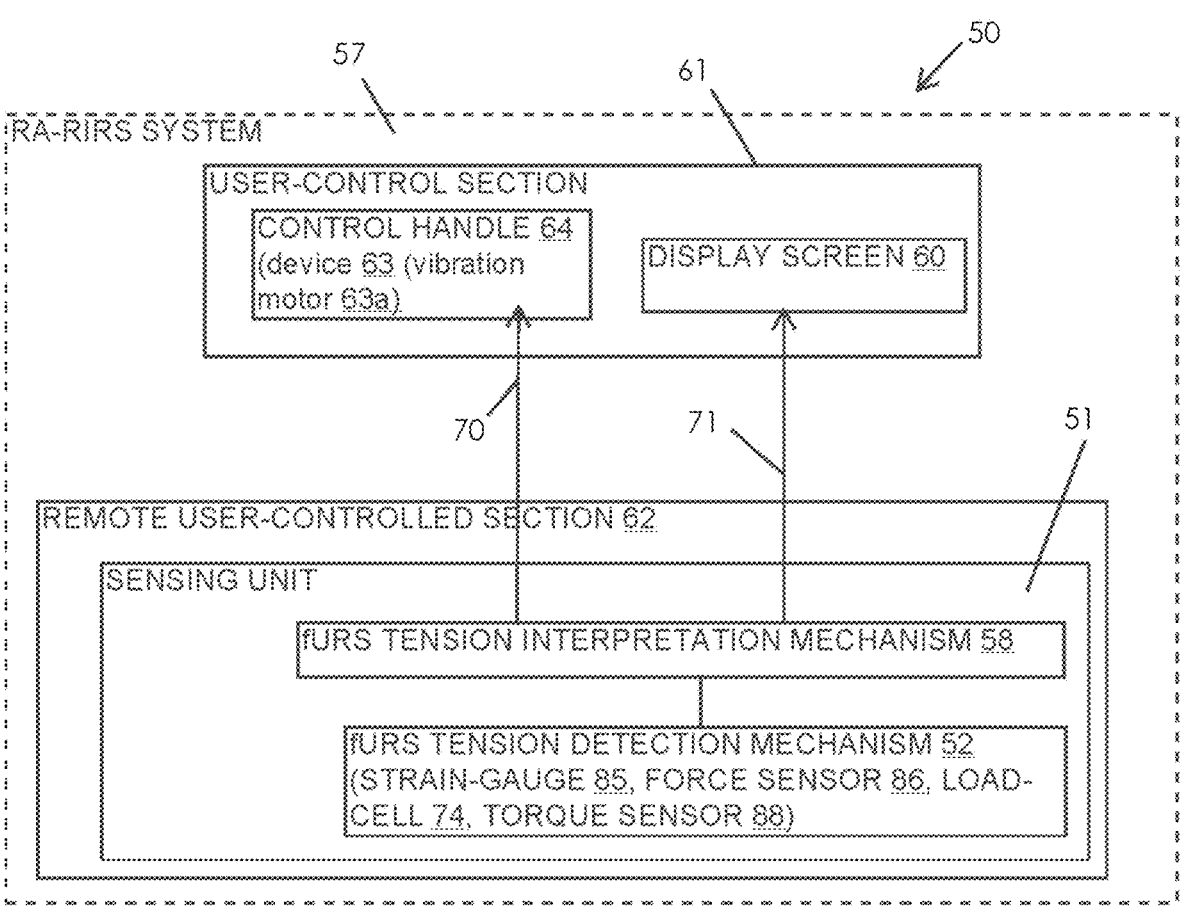
FIG. 9 is a schematic block diagram showing the interrelationship between selected components of the present disclosure.

In a non-limiting exemplary embodiment(s), the fURS tension detection mechanism 52 includes a load-cell 74 configured to detect the detected tension at shaft 55 of the fURS RA-RIRS system 57. For example, the load-cell 74 converts the detection tension (e.g., tension, torque, compression, pressure, etc.) into an output signal. This output signal is then transmitted via a load cable to fURS tension interpretation mechanism 58 where a precise intensity level is measured (quantified). FIGS. 7-9 illustrate the interrelationship between the major electrical components as well as the control logic algorithm 90 for quantifying as well as selectively, chronologically, or contemporaneously providing visual and mechanical feedback signals 70, 71 to the user-control section 61 of the RA-RIRS system 57. Such a structural configuration yields the new, useful, and unpredicted result of selectively, chronologically, or contemporaneously providing, on a display screen 60 (monitor), (1) visual feedback 71 of the tension levels, as well as providing, on at least one control handle 64, (2) haptic feedback 70 of the tension levels. Thus, both the visual feedback 71 and the haptic feedback 70 selectively, chronologically, or contemporaneously occur at user interfaces of a robotic-assisted retrograde intra renal surgical (RA-RIRS) system 57.

In a non-limiting exemplary embodiment(s), the fURS tension detection mechanism 52 includes a torque sensor 88 configured to detect the detected tension. Such a structural configuration yields the new, useful, and unpredicted result of selectively, chronologically, or contemporaneously providing, on a display screen 60 (monitor), (1) visual feedback 71 of the tension levels, as well as providing, on at least one control handle 64, (2) haptic feedback 70 of the tension levels. Thus, both the visual feedback 71 and the haptic feedback 70 selectively, chronologically, or contemporaneously occur at user interfaces of a robotic-assisted retrograde intra renal surgical (RA-RIRS) system 57.

In a non-limiting exemplary embodiment(s), the sensing unit 51 is configured to be mechanically retrofitted directly to the existing fURS shaft 55. Such a structural configuration yields the new, useful, and unpredicted result of selectively, chronologically, or contemporaneously providing, on a display screen 60 (monitor), (1) visual feedback 71 of the tension levels, as well as providing, on at least one control handle 64, (2) haptic feedback 70 of the tension levels. Thus, both the visual feedback 71 and the haptic feedback 70 selectively, chronologically, or contemporaneously occur at user interfaces of a robotic-assisted retrograde intra renal surgical (RA-RIRS) system 57.

In a non-limiting exemplary embodiment(s), the fURS tension detection mechanism 52 includes an arm 53 and a clamp 54 attached thereto. The clamp 54 is configured to directly engage the existing fURS shaft 55 while the arm 53 is communicatively coupled to the load-cell 74. Such a structural configuration yields the new, useful, and unpredicted result of selectively, chronologically, or contemporaneously providing, on a display screen 60 (monitor), (1) visual feedback 71 of the tension levels, as well as providing, on at least one control handle 64, (2) haptic feedback 70 of the tension levels. Thus, both the visual feedback 71 and the haptic feedback 70 selectively, chronologically, or contemporaneously occur at user interfaces of a robotic-assisted retrograde intra renal surgical (RA-RIRS) system 57.

While various embodiments have been described, the description is intended to be exemplary, rather than limiting, and it is understood that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various examples for the purpose of streamlining the disclosure. This method of disclosure is not to be interpreted as reflecting an intention that the claims require more features than are expressly recited in each claim. Rather, as the following claims reflect, inventive subject matter lies in less than all features of a single disclosed example. Thus, the following claims are hereby incorporated into the Detailed Description, with each claim standing on its own as a separately claimed subject matter.

What is claimed as new and what is desired to secure by Letters Patent of the United States is:

1. A flexible ureteroscope (fURS) haptic feedback mechanism for providing haptic feedback at an existing robotic-assisted retrograde intra renal surgical (RA-RIRS) system, said fURS haptic feedback mechanism comprising:
   a sensing unit configured to be retrofitted to an existing controlled section of a robotic-assisted retrograde intra renal surgical (RA-RIRS) system that manipulates an existing fURS shaft, said sensing unit including
      a fURS tension detection mechanism being configured to detect tension at the existing fURS shaft, during a RA-RIRS surgical procedure, located at the existing controlled section of the RA-RIRS system, and
      a fURS tension interpretation mechanism in communication with said fURS tension detection mechanism and being configured to receive, evaluate, and quantify said detected tension;
   wherein said fURS tension interpretation mechanism is further configured to contemporaneously generate and transmit
      a visual feedback signal to an existing control section of the existing RA-RIRS system and thereby visually display, on an existing display screen of the existing RA-RIRS system, a quantified intensity level of said detected tension at the existing fURS shaft, and
      a haptic feedback signal to the existing control section of the existing RA-RIRS system and thereby mechanically emit, at an existing control handle of the existing RA-RIRS system, said quantified intensity level of said detected tension at the existing fURS shaft;
   wherein said existing display screen and said existing control handle are both physically located at a user-control section of the existing RA-RIRS system, wherein said user-control section is remotely located away from said sensing unit and physically spaced from said sensing unit;
   wherein said existing display screen and said existing control handle are both separated from said existing controlled section and said existing fURS shaft as well as remotely located from said existing controlled section and said existing fURS shaft;
   wherein said sensing unit is configured to be mechanically retrofitted to the existing fURS shaft.

2. The fURS haptic feedback mechanism of claim 1, wherein said visual feedback signal and said haptic feedback signal are simultaneously transmitted to the existing control section of the existing RA-RIRS system.

3. The fURS haptic feedback mechanism of claim 1, wherein said visual feedback signal is graphically illustrated on the existing display screen.

4. The fURS haptic feedback mechanism of claim 1, wherein said haptic feedback signal is mechanically emitted at the existing control handle of the existing RA-RIRS system.

5. The fURS haptic feedback mechanism of claim 1, wherein said fURS tension detection mechanism comprises: a strain-gauge configured to detect said detected tension.

6. The fURS haptic feedback mechanism of claim 1, wherein said fURS tension detection mechanism comprises: a force sensor configured to detect said detected tension.

7. The fURS haptic feedback mechanism of claim 1, wherein said fURS tension detection mechanism comprises: a load-cell configured to detect said detected tension.

8. The fURS haptic feedback mechanism of claim 1, wherein said fURS tension detection mechanism comprises: a torque sensor configured to detect said detected tension.

9. A flexible ureteroscope (fURS) haptic feedback mechanism for providing haptic feedback at an existing robotic-assisted retrograde intra renal surgical (RA-RIRS) system, said fURS haptic feedback mechanism comprising:
   a sensing unit configured to be retrofitted to an existing controlled section of a robotic-assisted retrograde intra renal surgical (RA-RIRS) system that manipulates an existing fURS shaft, said sensing unit including
      a fURS tension detection mechanism being configured to detect tension at the existing fURS shaft, during a RA-RIRS surgical procedure, located at the existing controlled section of the RA-RIRS system, and
      a fURS tension interpretation mechanism in communication with said fURS tension detection mechanism and being configured to receive, evaluate, and quantify said detected tension;
   wherein said fURS tension interpretation mechanism is further configured to contemporaneously generate and transmit
      a visual feedback signal to an existing user-control section of the existing RA-RIRS system and thereby visually display, on an existing display screen of the existing RA-RIRS system, a quantified intensity level of said detected tension at the existing fURS shaft, and
      a haptic feedback signal to the existing user-control section of the existing RA-RIRS system and thereby mechanically emit, at an existing control handle of the existing RA-RIRS system, said quantified intensity level of said detected tension at the existing fURS shaft;

wherein said fURS tension detection mechanism includes
a load-cell positioned inside the sensing unit and being configured to detect said detected tension,
an arm, and
a clamp attached to said arm;
wherein said clamp is configured to directly engage the existing fURS shaft while said arm is communicatively coupled to said load-cell;
wherein said sensing unit is configured to be mechanically retrofitted to the existing fURS shaft.

10. The fURS haptic feedback mechanism of claim 9, wherein said visual feedback signal and said haptic feedback signal are simultaneously transmitted to the existing user-control section of the existing RA-RIRS system.

11. The fURS haptic feedback mechanism of claim 9, wherein said visual feedback signal is graphically illustrated on the existing display screen.

12. The fURS haptic feedback mechanism of claim 9, wherein said haptic feedback signal is mechanically emitted at the existing control handle of the existing RA-RIRS system.

13. A flexible ureteroscope (fURS) haptic feedback mechanism for providing haptic feedback at an existing robotic-assisted retrograde intra renal surgical (RA-RIRS) system, said fURS haptic feedback mechanism comprising:
a sensing unit configured to be retrofitted to an existing controlled section of a robotic-assisted retrograde intra renal surgical (RA-RIRS) system that manipulates an existing fURS shaft, said sensing unit including
a fURS tension detection mechanism being configured to detect tension at the existing fURS shaft, during a RA-RIRS surgical procedure, located at the existing controlled section of the RA-RIRS system, and a fURS tension interpretation mechanism in communication with said fURS tension detection mechanism and being configured to receive, evaluate, and quantify said detected tension;

wherein said fURS tension interpretation mechanism is further configured to contemporaneously generate and transmit
a visual feedback signal to an existing user-control section of the existing RA-RIRS system and thereby visually display, on an existing display screen of the existing RA-RIRS system, a quantified intensity level of said detected tension at the existing fURS shaft, and
a haptic feedback signal to the existing user-control section of the existing RA-RIRS system and thereby mechanically emit, at an existing control handle of the existing RA-RIRS system, said quantified intensity level of said detected tension at the existing fURS shaft;

wherein said fURS tension detection mechanism includes
a load-cell positioned inside the sensing unit and being configured to detect said detected tension,
an arm, and
a clamp attached to said arm;
wherein said clamp is configured to directly engage the existing fURS shaft while said arm is communicatively coupled to said load-cell;
wherein said arm is directly connected to said clamp and said sensing unit, respectively;
wherein said arm has a curvilinear shape and is intercalated between said clamp and said sensing unit;
wherein said sensing unit is configured to be mechanically retrofitted to the existing fURS shaft.

* * * * *